Figure 1:
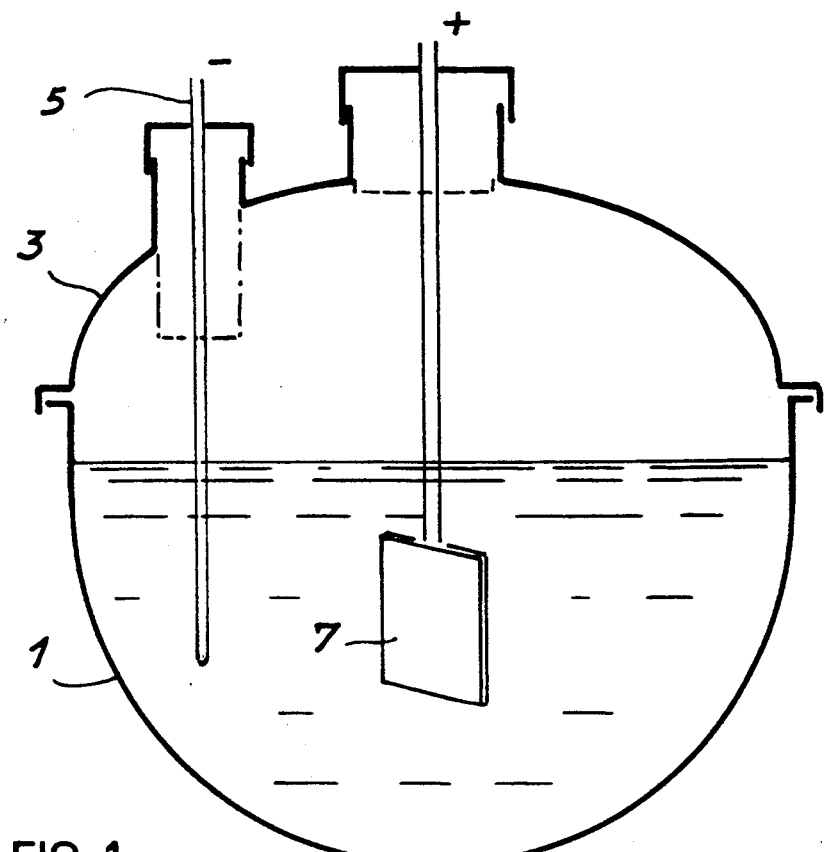

United States Patent [19]

Moussavi

[11] Patent Number: 5,112,597
[45] Date of Patent: May 12, 1992

[54] RADICAL LITHIUM PHTHALOCYANINE CRYSTALS, THEIR PREPARATION PROCESS AND THEIR USE FOR THE IN VIVO DETERMINATION OF MOLECULAR OXYGEN

[75] Inventor: Mehdi Moussavi, Saint Egreve, France

[73] Assignee: Commissariat a l'Energie Atomique, Paris, France

[21] Appl. No.: 723,243

[22] Filed: Jun. 28, 1991

[30] Foreign Application Priority Data

Jul. 10, 1990 [FR] France ................. 90 08739

[51] Int. Cl.$^5$ ............ A61K 31/40; A61K 49/00; C07D 487/22
[52] U.S. Cl. ................ 424/9; 204/58 QM; 204/59 QM; 514/410; 540/139
[58] Field of Search .......... 424/9; 204/58 QM; 514/410; 540/139

[56] References Cited

U.S. PATENT DOCUMENTS 4,996,311  2/1991  Moussavi et al. ............. 540/139

Primary Examiner—Richard L. Raymond
Attorney, Agent, or Firm—Oblon, Spivak, McClelland, Maier & Neustadt

[57] ABSTRACT

The invention relates to novel radical lithium phthalocyanine crystals, their preparation process and their use for in vivo determination of molecular oxygen.

These radical lithium phthalocyanine crystals comply with the formula:

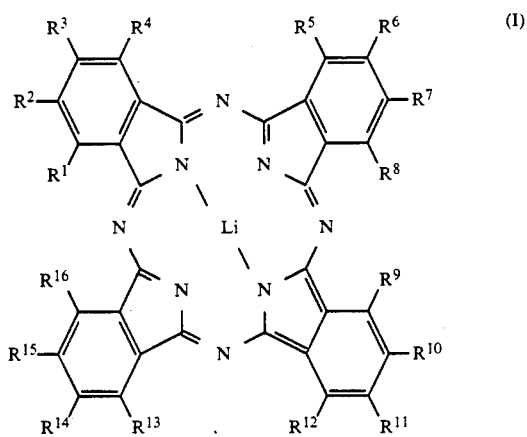

in which $R^1$ and $R^2$, which can be the same or different, represent a deuterium or hydrogen atom having a tetragonal crystalline structure belonging to the space group P4/mcc.

They are usable for in vivo oxygen determination by EPR spectrometry.

7 Claims, 3 Drawing Sheets

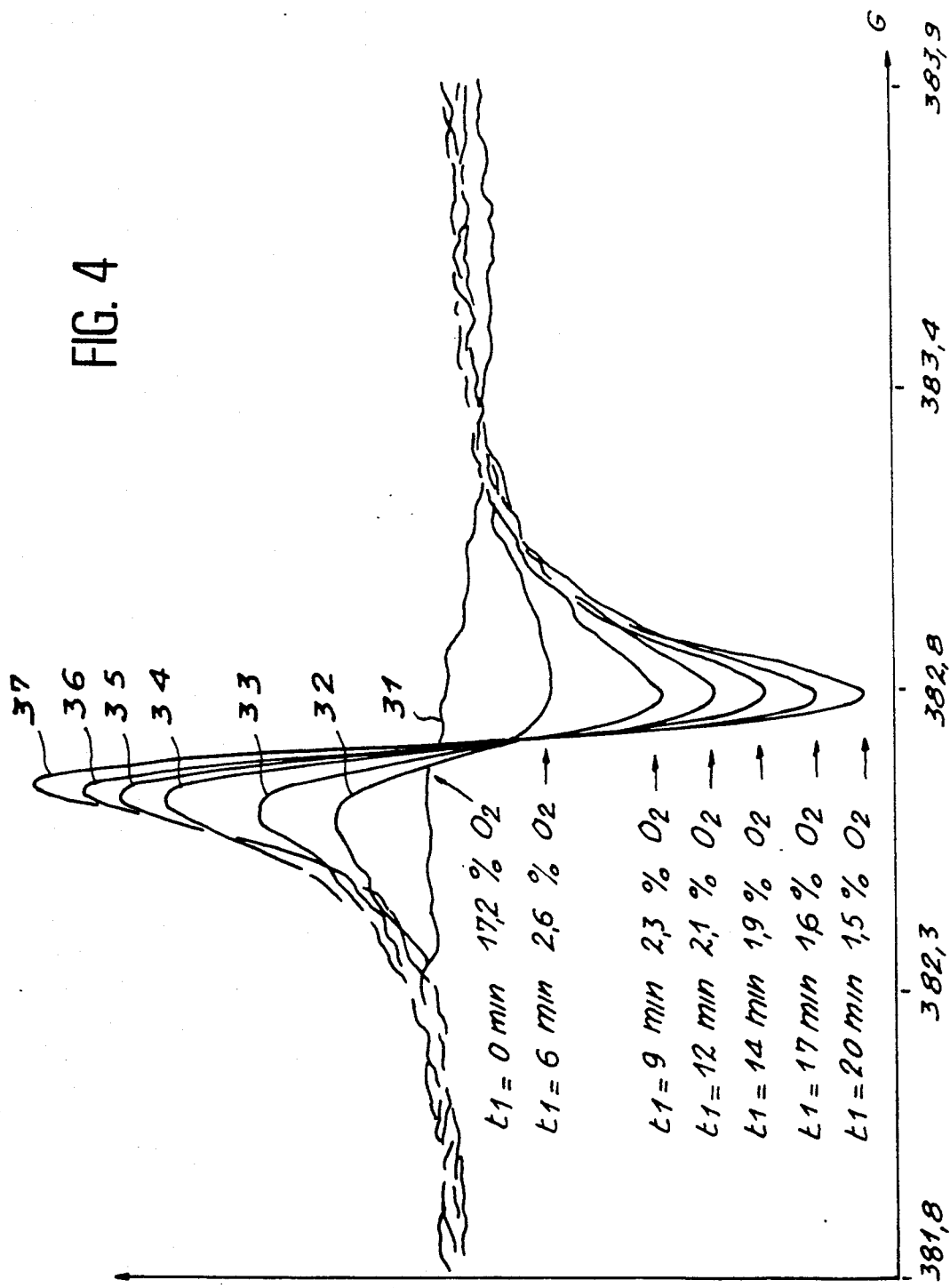

RADICAL LITHIUM PHTHALOCYANINE CRYSTALS, THEIR PREPARATION PROCESS AND THEIR USE FOR THE IN VIVO DETERMINATION OF MOLECULAR OXYGEN

The present invention relates to novel radical lithium phthalocyanine crystals. More specifically, it relates to radical lithium phthalocyanine crystals having improved properties compared with existing radical lithium phthalocyanine crystals and which are suitable for the determination or estimation of molecular oxygen by means of an electronic paramagnetic resonance (EPR) spectrometer under good conditions.

Recently development has taken place of processes for measuring the molecular oxygen concentration of cells by electronic paramagnetic resonance (EPR). In these processes, use is made of a radical tracer, whose EPR characteristics (mainly the line width) vary as a function of the oxygen content of the medium in which the radical tracer is located. Procedures for determining molecular oxygen by EPR spectrometry are e.g. described in Swartz, Pure & Appl. Chem., Vol. 62, No. 2, pp. 235-239, 1990; and Woods et al, Journal of Magnetic Resonance, No. 85, pp. 50-59, 1989.

In order to measure the intracellular oxygen concentration by this procedure, a radical substance is injected or implanted in the medium or organ whose oxygen content is to be established and then this substance is examined whilst it is immersed in the said medium using an electronic paramagnetic resonance spectrometer. On the basis of the EPR line width obtained, it is possible to deduce the oxygen content of the medium by referring to a predetermined calibration curve of a sample of the radical substance giving the relation between the EPR line width and the oxygen content.

The radical substances used in such processes must have different properties. Thus, they must be biocompatible and have EPR characteristics which change as a function of the oxygen content of the medium, at least in the range of concentrations to be followed, which is 0 to 10% molecular oxygen in the case of human organs to be examined.

Hitherto, the radical substance used in such processes has been 2,2,6,6-tetramethyl piperidine-N-oxyl-4-one (TANO). However, it would be advantageous to have other radical substances for these processes, because the EPR characteristic variations of TANO in the most interesting oxygen concentration range (0 to 10% oxygen) are inadequate.

The present invention relates to a radical substance usable for the in vivo determination of oxygen by electronic paramagnetic resonance, which has more interesting characteristics than those of TANO in the concentration range between 0 and 10%.

This radical substance is constituted by radical lithium phthalocyanine crystals in accordance with the formula:

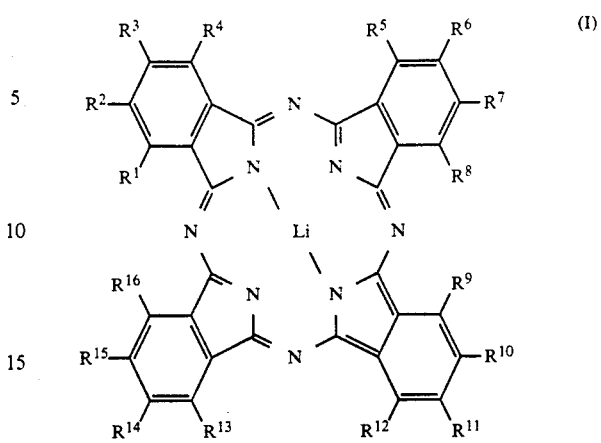

in which $R^1$ to $R^{16}$, which can be the same or different, represent a deuterium or hydrogen atom and have a tetragonal crystalline structure belonging to the space group P4/mcc.

According to a first embodiment of the invention all the $R^1$ to $R^{16}$ represent a hydrogen atom. In this case, the crystallographic parameters of phthalocyanine are as follows:
a:13.850 Å
b:13.850 Å
c:6.403 Å
$\alpha$:90°
$\beta$:90°
$\gamma$:90°
Mesh volume:1228 Å$^3$.

The radical lithium phthalocyanine of formula (I) in which $R^1$ to $R^{16}$ are hydrogen atoms is a radical substance which has been known for some time, but which up to now has never been obtained in the form of crystals having a tetragonal structure belonging to the space group P4/mcc.

Thus, the known radical lithium phthalocyanine crystals have a tetragonal structure belonging to the space group P4/nnc. However, this difference is important, because the particular crystalline structure (tetragonal, space group P4/mcc) of the radical lithium phthalocyanine according to the invention gives it much more interesting EPR characteristics for molecular oxygen determination.

Thus, the width of the EPR line of the radical lithium phthalocyanine according to the invention is only 2000nT, whereas it is 30,000nT in the case of the tetragonal radical lithium phthalocyanine belonging to the space group P4/nnc.

Moreover, with the radical phthalocyanine according to the invention, the EPR line width varies substantially linearly with the oxygen content in the concentration range between 0 and 10%, whereas the EPR line width of the prior art phthalocyanine virtually does not vary with the oxygen content.

As a result of these characteristics, it is possible to obtain with the phthalocyanine crystals according to the invention a better accuracy when measuring low oxygen contents in biological tissues. Moreover, the high sensitivity of the crystals to oxygen makes it possible either to inject smaller radical substance quantities if this proves to be necessary, or to reduce the acquisition time for the EPR curves and thus obtain a faster response to the metabolisms of organs.

According to a second embodiment of the invention, the lithium phthalocyanine of formula (I) is at least partly substituted by deuterium atoms. In this case even better results are obtained through the presence of deuterium atoms.

Generally, the substitution relates to at least one of the positions $R^1$, $R^4$, $R^5$, $R^8$, $R^9$, $R^{12}$, $R^{13}$ and $R^{16}$ of formula (I), because it is more difficult to substitute by deuterium hydrogen atoms in the following positions $R^2$, $R^3$, $R^6$, $R^7$, $R^{10}$, $R^{11}$, $R^{14}$ and $R^{15}$.

The radical lithium phthalocyanine crystals according to formula (I) can be obtained by a process consisting of galvanostatically monoelectronically oxidizing the dilithiated lithium phthalocyanine of formula:

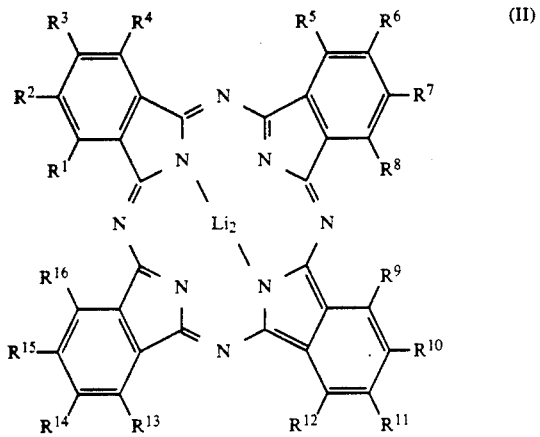

in which $R^1$ to $R^{16}$ have the meanings given hereinbefore, in solution in acetonitrile containing at the most 50 ppm water and using an anode constituted by a platinum plate, a cathode constituted by a platinum wire and a support electrolyte constituted by tetrabutyl ammonium perchlorate or hexafluorophosphate.

In this process, oxidation is carried out galvanostatically, i.e. with a constant current, but it is possible to operate in ranges by carrying out several stages at constant current, but with different current intensities between the individual stages. It is possible in this way to control the crystal growth kinetics or bring about a system evolution between states of equilibrium when several ranges are used and in this way obtain the sought crystalline form.

Conventionally the radical lithium phthalocyanine has been prepared by monoelectronically oxidizing the dilithiated lithium phthalocyanine, but using the potentiostatic method, i.e. a constant potential, which leads to a good efficiency level. However, in this case the electrolysis kinetics are not controlled and a powder having poorly defined and poorly shaped crystals are obtained, which do not correspond to the crystalline needles according to the invention.

In order to obtain this particular crystalline shape, it is also necessary to choose a solvent, a support electrolyte and electrodes of an appropriate nature.

As stated hereinbefore, the appropriate solvent is acetonitrile containing at the most 50 ppm of water and which has preferably been purified with respect to the acetic acid traces therein, e.g. by passing over an alumina column.

Thus, the desired crystalline structure is not obtained when working with another solvent, such as acetone.

The suitable electrodes are platinum electrodes and the support electrolyte can be tetrabutyl ammonium hexafluorophosphate (or perchlorate). It is also preferable for the electrolytic cell to be hemispherical.

In the case that it is wished to obtain deuterated radical lithium phthalocyanine crystals, the same procedure is used, but the starting product is deuterated, dilithiated lithium phthalocyanate. The latter can be obtained by H-D isotopic exchange between dilithiated phthalocyanine and deuterated tetramethyl pyridine in the presence of a lithiated, deuterated tetramethyl pyridine-based catalyst.

The radical lithium phthalocyanine crystals according to the invention can in particular be used for molecular oxygen determination.

The invention also relates to a process for the determination of molecular oxygen in a medium such as a liquid or a gas, which consists of contacting the said medium with at least one radical lithium phthalocyanine crystal according to the invention and then determining the width of the EPR line of said crystal.

The radical lithium phthalocyanines according to the invention can also be used for the in vivo determination of molecular oxygen, e.g. in the heart or other organs with a view to detecting diseased cells of said organs, i.e. those having below normal oxygen contents.

In order to carry out such in vivo examinations, it is possible to implant the radical phthalocyanine crystals according to the invention directly in the organ to be examined, or to use a suspension of these crystals in an organic liquid injected into the patient to be examined.

The liquids used for preparing such suspensions are non-toxic, bio-compatible liquids, e.g. alcohols such as furfuryl alcohol, $C_4$ to $C_{10}$ alcohols and polyalcohols. It is also possible to use veratrol.

If necessary, the suspension can contain other additives, such as agents stabilizing the suspension or regulating its viscosity to an appropriate value.

The phthalocyanine concentration of the suspension can vary within a wide range and is preferably between 0.1 and 10 mg/l.

Although the radical lithium phthalocyanines according to the invention are not toxic, the administered doses are generally very low and can e.g. be 0.01 to 0.1 mg/kg of body weight.

Following the implantation of the crystals or the administration of the suspension, it is rapidly possible to carry out the examination by EPR spectrometry.

The invention is described in greater detail hereinafter relative to non-limitative embodiments and the attached drawings, wherein show:

FIG. 1 diagrammatically an electrolytic cell usable for preparing the crystals according to the invention.

Figure 2:
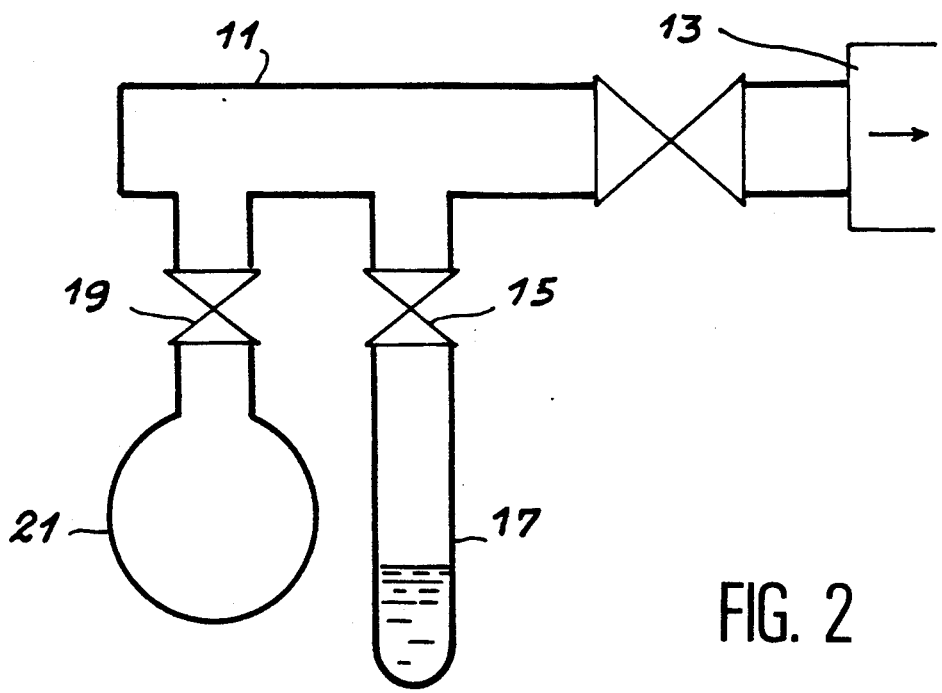

FIG. 2 diagrammatically an apparatus suitable for producing the calibration curve of the radical substance used.

Figure 3:
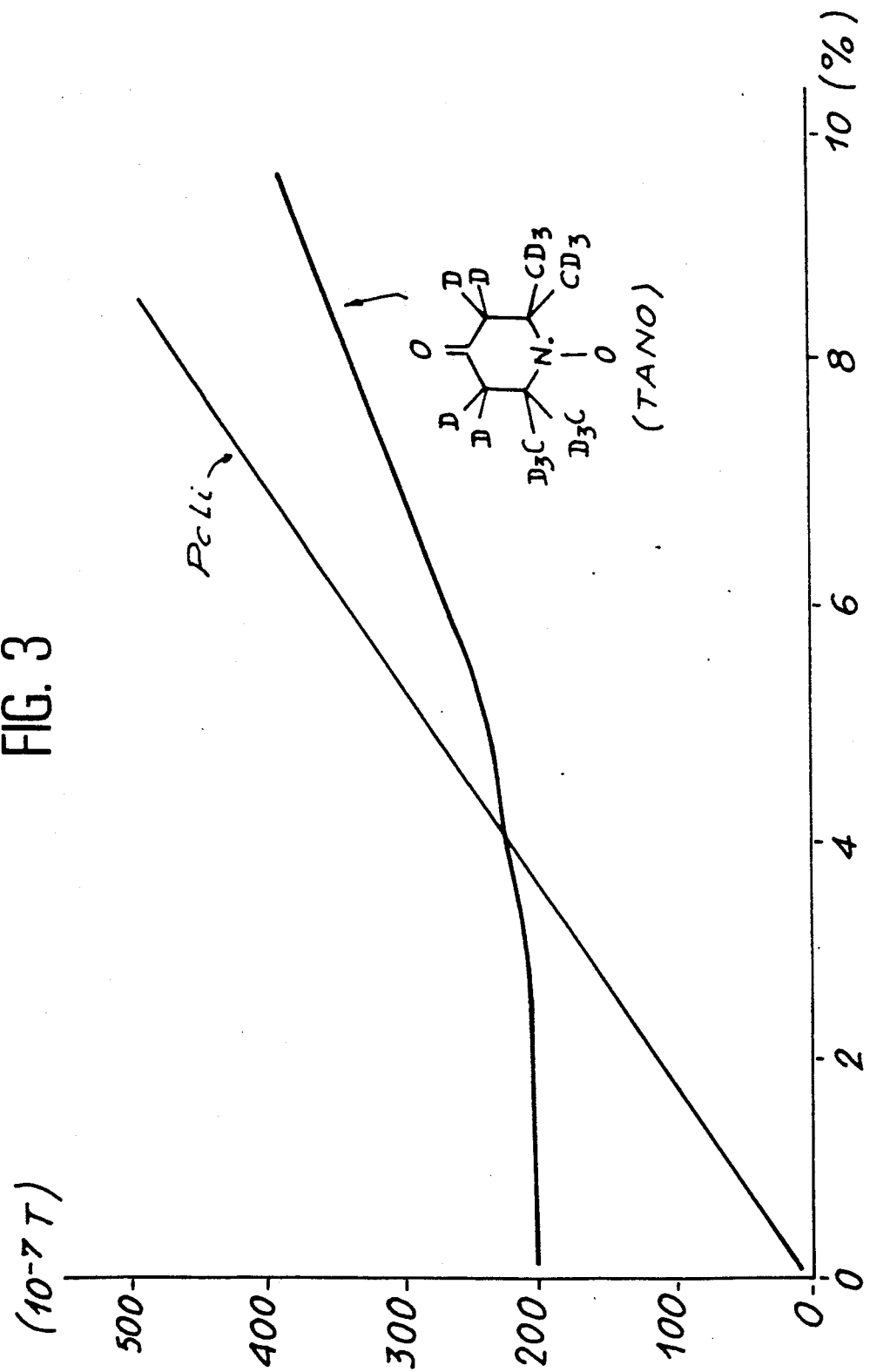

FIG. 3 a graph representing the variations of the EPR line width as a function of the oxygen content for the lithium phthalocyanine according to the invention (PcLi) and for a radical substance used in the prior art (TANO).

FIG. 4 a graph representing the variations of the EPR resonance line of lithium phthalocyanine during an experiment on the rat.

FIG. 1 diagrammatically shows an electrolytic cell usable for preparing radical lithium phthalocyanine crystals according to the invention. The cell (1) is hemispherical and is tightly sealed by a cover (3). Within the cell are placed a cathode (5) constituted by a metallic platinum wire e.g. having a diameter of 1 mm and a length of 4 cm, as well as an anode (7) constituted by a 25×35 mm platinum plate. The anode and the cathode are connected to an electric current generator equipped with a device making it possible to operate the cell according to the galvanostatic or intensiostatid procedure.

EXAMPLE 1

Preparation of lithium phthalocyanine crystals according to the invention

Into the cell (1) are introduced 300 mg of dilithiated phthalocyanine dissolved in 500 ml of ultra-anhydrous acetonitrile. The acetonitrile used has a water content below 50 ppm and, just prior to use, it is passed over an activity I basic alumina powder column with a diameter of 5 cm and a height of 10 cm, in order to eliminate any acetic acid traces which may be contained therein. Into the cell are also introduced 400 mg of a support electrolyte constituted by tetrabutyl ammonium hexafluorophosphate, which has been recrystallized five times in ethanol and dried for 24h in vacuo at 80° C.

After sealing the electrolytic cell, electrosynthesis is carried out using a constant current of $5\mu A$ for 24h, then a constant current of $20\mu A$ for 48h and a constant current of $50\mu A$ for 72h.

At the end of the operation, 150 mg of radical lithium phthalocyanine are collected in the form of black monocrystalline needles having the crystalline characteristics given in Table 1.

EXAMPLE 2

In this example determinaton takes place of the EPR characteristics of the crystals of Example 1 in the presence of different oxygen concentrations in order to obtain the calibration curve corresponding to the EPR line width variations as a function of the oxygen content of the medium.

To this end, the previously obtained lithium phthalocyanine crystals are introduced into a tube, in which a vacuum is formed and the width of the EPR line is measured after introducing the tube, maintained in vacuo, into an EPR spectrometer. The same measurements are then repeated after contacting the crystals with different oxygen quantities.

This can be carried out by using the device diagrammatically shown in FIG. 2, which comprises a vacuum system (11) equipped with a pumping group (13) for forming the vacuum in the system and which can be connected via a valve (15) to a tube (17) containing the lithium phthalocyanine crystals and by a valve (19) to a container (21) containing a given oxygen volume.

In order to carry out the first measurement, the valve (15) is opened after placing the tube (17) on the apparatus and forming the vacuum with the pumping group (13). The valve (15) is then closed again and the sealed tube (17) is introduced into the EPR spectrometer. Following this measurement, the tube (17) is again placed on the vacuum system (11). The valve (15) and the valve (19) are then opened for contacting the lithium phthalocyanine with the given oxygen volume of the container (21). Following said contacting, valve (15) is closed and the tube (17) is introduced into the EPR spectrometer to obtain the line width at 9GHz.

Following this operation, the lithium phthalocyanine is again degassed by placing the tube (17) on the vacuum system (11) and by producing a vacuum in the installation. The degassed phthalocyanine is then contacted with another oxygen volume using another container (21). Thus, the EPR line width values are obtained as a function of the oxygen concentration.

FIG. 3 shows in continuous line form the said curve of the EPR line width variations (in $10^{-7}$ T) as a function of the oxygen content (in %).

In FIG. 3 it can be seen that the line width variation is substantially linear in the concentration range from 0 to 10% and that it is possible to detect very small oxygen content variations in said concentration range.

For comparison purposes (in pecked line form) are shown the EPR line width variations obtained under the same conditions with TANO, which was previously used for EPR oxygen determination.

On comparing the two curves, it can be seen that TANO does not make it possible to detect oxygen concentration variations in the range 0 to 6%, which clearly demonstrates the interest of the invention.

COMPARATIVE EXAMPLE 1

In this example preparation takes place of radical lithium phthalocyanine from the same dilithiated lithium phthalocyanine as that used in Example 1, but electrochemical oxidation takes place potentiostatically in acetone at $+0.5V$. In this way tetragonal phthalocyanine crystals are obtained, which belong to the space group P4/nnc having the crystallographic characteristics given in Table 1.

This is followed by the determination of the EPR line width of said lithium phthalocyanine by operating under the same conditions as in Example 1. It is found that the line width is 30,000nT, which is well above that obtained with the lithium phthalocyanine according to the invention. In addition, said line width does not vary with the oxygen content of the medium.

Thus, the lithium phthalocyanIne according to the prior art cannot be used for determining molecular oxygen.

EXAMPLE 3

In this example use is made of the lithium phthalocyanine crystals obtained in Example 1 for examining the evolution of the oxygen level in the heart of a rat. For this purpose the rat is anesthetized and in its heart is implanted a crystal of the radical lithium Phthalocyanine of Example 1. The rat is then sacrificed and its heart removed and is introduced into an EPR spectrometer.

The signal obtained just following the introduction of the heart into the spectrometer is examined at 1 GHz, followed by the EPR signal obtained after 6 minutes and then those obtained every 3 minutes.

The results obtained are given in FIG. 4, where curve 31 refers to the signal obtained at time 0, curve 32 to that obtained after 6 min. and curves 33,34,35,36 and 37 respectively to the signals obtained after 9, 12, 14, 17 and 20 min.

These results show that the oxygen concentration, which was initially 17.2%, drops to 1.5% after 20 min. and that these variations can easily be followed by examining the EPR signal.

Therefore the lithium phthalocyanine crystals according to the invention can be used for intracellular oxygen determination.

The following example illustrates the preparation of a suspension of these crystals usable for the determination of oxgyen in living beings.

EXAMPLE 4

1 mg of the radical lithium phthalocyanine crystals obtained in Example 1 is introduced into a glass tube containing 10 ml of hexanol. The tube content is then frozen in liquid nitrogen, followed by degassing by pumping under a secondary vacuum ($10^{-4}$ Pa) for 30 minutes, after which the tube is sealed. In order to make the mixture homogeneous, the sealed tube is introduced into an ultrasonic tank for 15 min.

During use, the tube is opened under an inert atmosphere, e.g. in a glove box and using a tight syringe 0.1 to 0.5 ml of the suspension is sampled ready for injection into the organ to be studied.

According to a variant, it is possible to use bottles having a crimpable end similar to pharmaceutical injectable solute bottles, which are sealed by an aluminium cap provided with a rubber packing. In this case, degassing can be carried out by bubbling argon into the bottle at a rate of 4 l/h for 20 min. for 10 ml of suspension.

TABLE 1

| Radical substance | PcLi (ex. 1) | PcLi (comparative ex. 1) |
|---|---|---|
| (EPR line width) | 2 000 nT | 30 000 nT |
| Space group | tetragonal P4/mcc | tetragonal P4/nnc |
| a (Å) | 13.850 | 19.576 |
| b (Å) | 13.850 | 19.576 |
| c (Å) | 6.403 | 6.407 |
| α (degrees) | 90 | 90 |
| β (degrees) | 90 | 90 |
| γ (degrees) | 90 | 90 |
| mesh volume (Å$^3$) | 1228 | 2455 |

I claim:

1. Radical lithium phthalocyanine crystals according to the formula:

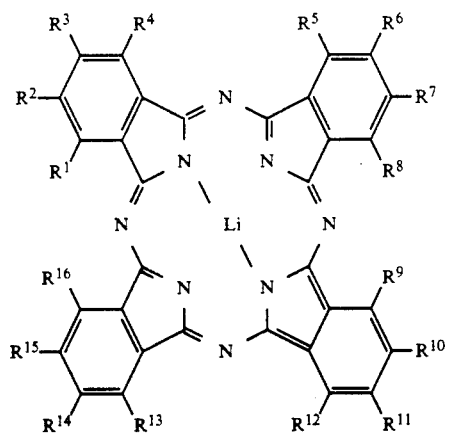

(I)

in which $R^1$ to $R^{16}$ which can be the same or different, represent a deuterium or hydrogen atom and have a tetragonal crystalline structure belonging to the space group P4/mcc.

2. Radical phthalocyanine crystals according to claim 1, characterized in that the $R^1$ to $R^{16}$ represent a hydrogen atom.

3. Radical lithium phthalocyanine crystals according to claim 1, characterized in that $R^2$, $R^3$, $R^6$, $R^7$, $R^{10}$, $R^{11}$, $R^{14}$ and $R^{15}$ represent a hydrogen atom and at least one of the $R^1$, $R^4$, $R^5$, $R^8$, $R^9$, $R^{12}$, $R^{13}$ and $R^{16}$ represents a deuterium atom.

4. Radical lithium phthalocyanine crystals according to claim 2, characterized in that their crystallographic parameters are as follows:
a:13.850 Å
b:13.850 Å
c:6.403 Å
α:90°
β:90°
γ:90°
Mesh volume:1228 Å$^3$.

5. Process for the preparation of radical lithium phthalocyanine crystals according to any one of the claims 1 to 4, characterized in that it consists of galvanostatically monoelectronically oxidizing the dilithiated lithium phthalocyanine of formula:

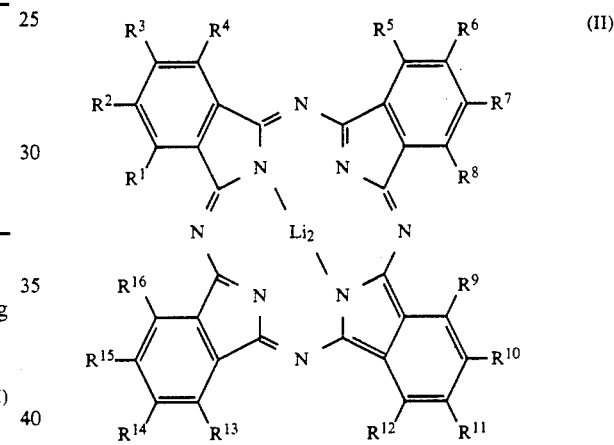

(II)

in which $R^1$ to $R^{16}$ have the meanings given in claim 1, in solution in acetonitrile containing at the most 50 ppm of water, using an anode constituted by a platinum plate, a cathode constituted by a platinum wire and a support electrolyte constituted by tetrabutyl ammonium perchlorate or hexafluorophosphate.

6. Process for determining molecular oxygen in a medium, characterized in that it consists of contacting the said medium with a radical lithium phthalocyanine crystal according to any one of the claims 1 to 4 and determining the electronic paramagnetic resonance (EPR) line width of said radical lithium phthalocyanine crystal.

7. Composition for the in vivo determination of molecular oxygen, characterized in that it is constituted by a suspension of radical lithium phthalocyanine crystals according to any one of the claims 1 to 4 in a liquid.

* * * * *